US00PP24245P3

(12) United States Plant Patent
Randag

(10) Patent No.: US PP24,245 P3
(45) Date of Patent: Feb. 11, 2014

(54) VARIETY OF CALLA LILY NAMED 'ASPEN'

(50) Latin Name: *Zantedeschia sprengeri*
Varietal Denomination: Aspen

(75) Inventor: Cecilius Jan-Jochem Randag, Bosweg (NL)

(73) Assignee: Sande B.V., 't Zand (NL)

( * ) Notice: Subject to any disclaimer, the term of this patent is extended or adjusted under 35 U.S.C. 154(b) by 0 days.

(21) Appl. No.: 13/374,389

(22) Filed: Dec. 27, 2011

(65) Prior Publication Data

US 2013/0167278 P1 Jun. 27, 2013

(51) Int. Cl.
*A01H 5/00* (2006.01)

(52) U.S. Cl.
USPC ..... Plt./490

(58) Field of Classification Search
USPC ..... Plt./490
See application file for complete search history.

*Primary Examiner* — Kent L Bell
(74) *Attorney, Agent, or Firm* — The Webb Law Firm

(57) ABSTRACT

'Aspen' is a new variety of calla lily having inflorescences with a pure white-colored spathe that produces 2-10 inflorescences per tuber. The inflorescence stems are about 70 cm. in height and the leaves are green with whitish spots and have a leathery texture.

2 Drawing Sheets

Botanical classification: *Zantedeschia sprengeri.*
Varietal denomination: 'ASPEN'.

BACKGROUND OF THE NEW PLANT

The present invention comprises a new and distinct cultivar of calla lily, botanically known as *Zantedeschia sprengeri* and hereinafter referred to by the cultivar name 'Aspen'.

'Aspen' is a product of a planned breeding program which had the objective of creating *Zantedeschia* hybrids for cut inflorescence production in a wide range of colors with a large, classic inflorescence shape. The breeding program began in 1989 and the new cultivar is a seedling selected from the crossing of *Zantedeschia sprengeri* seedling Z030479 (female parent, unpatented) with *Zantedeschia sprengeri* variety 'Chrystal Blush' (male parent, unpatented). 'Aspen' was selected in 2008 by the inventor C. J. J. Randag in 't Zand, The Netherlands as one flowering plant within the progeny of the stated cross.

The first act of asexual reproduction of 'Aspen' by tissue culture was performed by the inventor in August of 2008 in 't Zand, The Netherlands. Further asexual reproductions by tissue culture at the same location has demonstrated that the combination of characteristics as herein disclosed for the new cultivar are retained and reproduced true to type through successive generations of asexual reproduction.

The following observations, measurements and comparisons describe plants grown in 't Zand, The Netherlands under greenhouse conditions which approximate those generally used in horticultural practice. Color references are made to The R.H.S. Colour Chart of The Royal Horticultural Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Apen' which, in combination, distinguish this calla lily as a new and distinct cultivar:

1. Pure white-colored spathe;
2. Fast forcing time; and
3. High inflorescence production.

Table 1 provides similarities and differences of 'Aspen' to its parents and 'Captain Ventura' (U.S. Plant Pat. No. 21,245).

TABLE 1

| 'Aspen' | Similarities | Differences |
|---|---|---|
| Z030479 | Leaf shape | Number of spathes |
| 'Chrystal Blush' | Leaf shape | Spots on leaves<br>Very small and late pink blush |
| 'Captain Ventura' | Leaf shape | Spathe color<br>Spathe shape |

BRIEF DESCRIPTION OF THE DRAWINGS

The accompanying photographic drawings illustrate the new variety, with the colors being as nearly true as is possible with color illustrations of this type.

DESCRIPTION OF THE PLANT

The Plant

Figure 1:
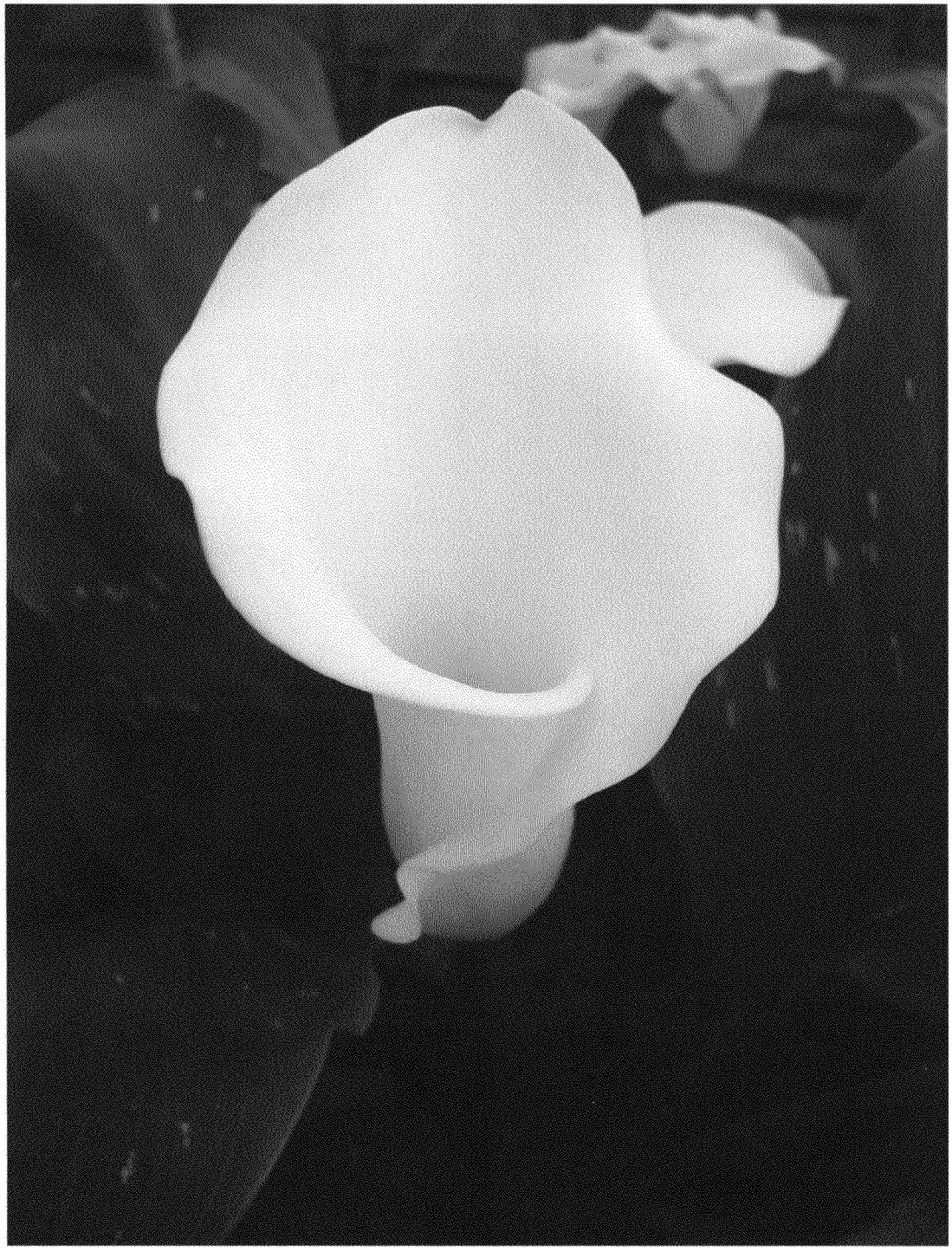
FIG. 1 is a close-up photograph of the new variety.
Figure 2:
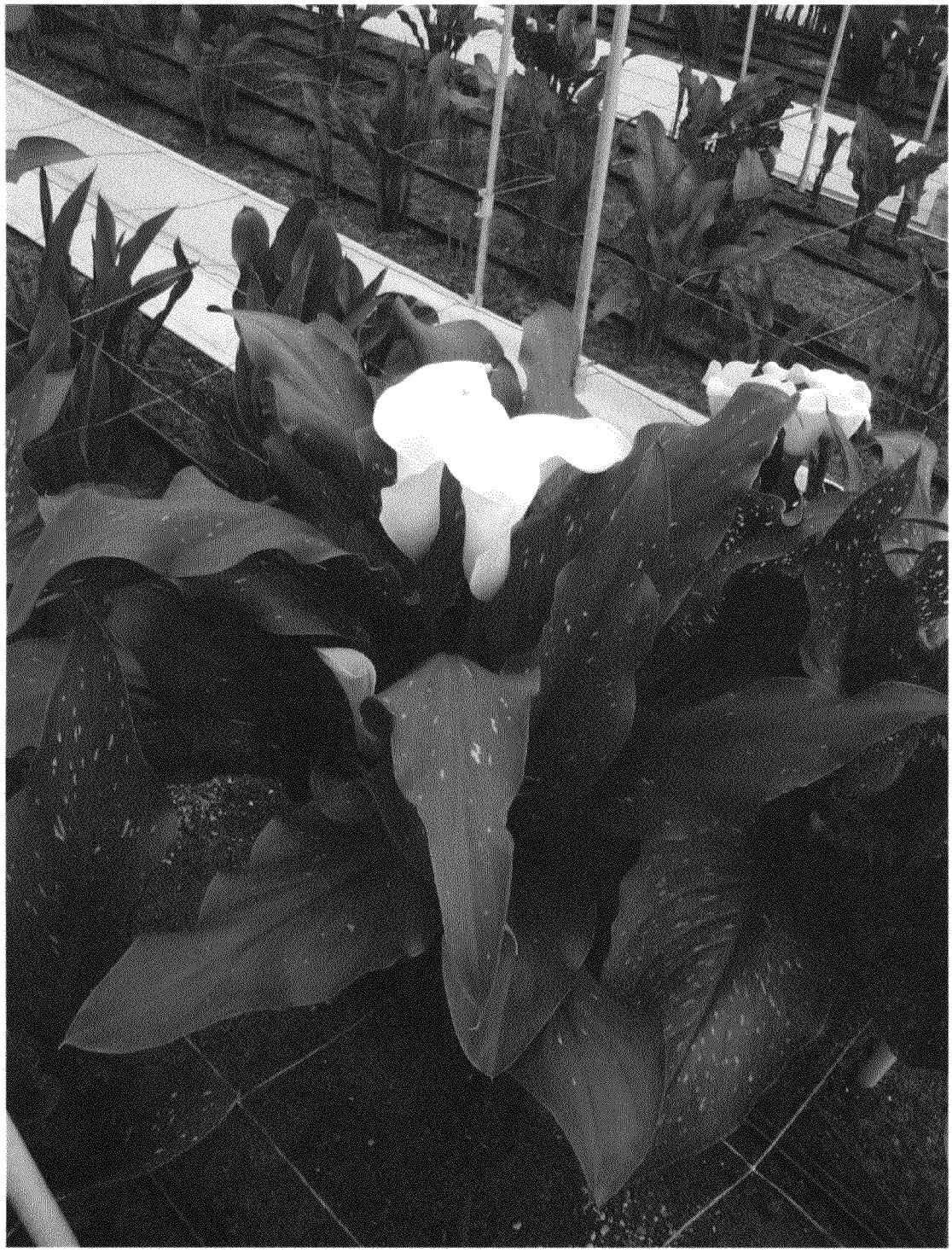
FIG. 2 is a photograph of multiple plants of the new variety.

Size:
*Height of the leaf canopy above the soil.*—70-85 cm.
*Height of top of inflorescence above the soil.*—70-95 cm.
*Diameter.*—25-40 cm.

Form: Erect.

Number of flowers per tuber:
*Size* 9-12 *cm. in diameter.*—2-4 inflorescences.
*Size* 12-15 *cm. in diameter.*—4-inflorescences.
*Size* 15-18 *cm. in diameter.*—6-10 inflorescences.

Branches:

*Character*.—Like the variety 'Picasso' (U.S. Plant Pat. No. 15,282).

*Color*.—Between Yellow-Green Group RHS 146A and 146B, with spots between Red-Purple Group RHS 59A and 59B.

Leaves:

*Size*.—Width: 7-9 cm. Length: 70-90 cm.

*Number per plant*.—10-20.

*Shape*.—Elliptic.

*Color*.—Upper surface: Green Group RHS 137C to 137D. Lower surface: Green Group RHS 137C to 137D.

*Apex*.—Apiculate.

*Base*.—Between obtuse and truncate.

*Margin*.—Undulate.

*Veins*.—Configuration: Pinnate. Color: Yellow-Green Group RHS 147B.

*Surface quality*.—Leathery.

*Petiole*.—Length: 50-65 cm. Diameter: 11 mm. Color: The base is between Green-White Group RHS 157A and 157B. Above the base the petiole is heavily spotted with colors between Red-Purple Group RHS 59A and 59B. The upper part of the petiole is between Yellow-Green Group RHS 144A and 144B.

Roots:

*Color*.—White.

*Branching*.—Similar to other *Zantedeschia* varieties.

The Inflorescence and Seeds

Spathe:

*Size*.—Length: 6-15 cm. Width: 4-9 cm.

*Color*.—Upper surface: Varies between White Group RHS 155B and 155C. Lower surface: Varies between White Group RHS 155B and 155C; a very small Red-Purple Group RHS 68A to 68B sometimes appears on the edge of the spathe when maturing.

*Vein color*.—Approximately Yellow-White Group RHS 158C.

*Shape*.—Cupped.

*Apex*.—Round.

*Base*.—Rounded.

*Margin*.—Entire.

*Texture* (*both surfaces*).—Leathery.

Spadix:

*Size*.—Length: 10-25 mm. Diameter: 2-5 mm.

*Color*.—Between Yellow-Orange Group RHS 16B and 16C.

*Position relative to spathe*.—Upright.

*Shape*.—Elongated.

*Apex*.—Rounded.

Peduncle:

*Size*.—Length: 70-95 cm. Diameter: 6-10 mm.

*Color*.—Upper part varies between Yellow-Green Group RHS 144A and 144B and the lower part is Green-White Group RHS 157D with spots between Red-Purple Group RHS 59A and 59B.

*Texture*.—Smooth.

Reproductive organs:

*Location of female organs*.—Basal position of the spadix.

*Location of male organs*.—Upper position of the spadix.

*Perianth*.—Conspicuous.

*Stamens*.—Presence: Not visible before pollen release. Number: More than 50. Pollen amount: Similar to 'Picasso'. Color: Between White Group RHS 155A and 155B.

*Anther*.—Shape: Round and wire-like. Length: Less than 1 mm. Color: Between White Group RHS 155A and 155B.

*Filament*.—Length: Less than 1 mm. Color: Between White Group RHS 155A and 155B.

*Pistil*.—Number: 30 to 50. Length beyond perianth: About 1 mm.

*Stigma*.—Shape: Round. Size: Less than 1 mm.

*Style*.—Length: Less than 1 mm. Color: Between Yellow-Green Group RHS 144A and 144B.

*Ovaries*.—Texture: Smooth. Length: Between 1 to 10 mm. Width: Between 1 to 10 mm. Color: Top color is between Yellow-Green Group RHS 144A and 144B; bottom color is between Green-White Group RHS 157C and 157D.

Seeds:

*Length*.—4-7 mm.

*Width*.—3-6 mm.

*Color*.—Between Yellow-Green Group RHS 150B and 150C.

*Amount*.—Between 1-100.

General

Disease resistance: No unusual susceptibility to diseases noticed to date.

Pest resistance: No unusual susceptibility to pests noticed to date.

Heat tolerance: No heat tolerance.

Hardiness: Not hardy.

Blooming: Tubers planted in a greenhouse in The Netherlands in February produce inflorescences in April. Tubers planted outdoors in The Netherlands in May produce inflorescences in July.

Lastingness: About two weeks on the plant and ten days off the plant.

Fragrance: None.

I claim:

1. A new and distinct variety of calla lily plant named 'Aspen' as herein described and illustrated.

* * * * *